US00PP20628P2

(12) United States Plant Patent
Whetman

(10) Patent No.: US PP20,628 P2
(45) Date of Patent: Jan. 5, 2010

(54) ***DIANTHUS* PLANT NAMED 'BRIGHT EYES'**

(50) Latin Name: *Dianthus×hybrida*
Varietal Denomination: BRIGHT EYES

(76) Inventor: John Whetman, Deerpark Farm, Chudleigh, Newton Abbey, Devon (GB) TQ13 0NH ( * ) Notice: Subject to any disclaimer, the term of this patent is extended or adjusted under 35 U.S.C. 154(b) by 0 days.

(21) Appl. No.: 12/228,982

(22) Filed: Aug. 18, 2008

(51) Int. Cl.
*A01H 5/00* (2006.01)

(52) U.S. Cl. ..... Plt./279

(58) Field of Classification Search ..... Plt./279
See application file for complete search history.

*Primary Examiner*—Annette H Para

(57) ABSTRACT

A new cultivar of *Dianthus* plant named 'BRIGHT EYES' that is characterized by compact habit, grey-green foliage, and double flowers that are predominantly white in color with deep plum-red centers. In combination these traits set 'BRIGHT EYES' apart from all other existing varieties of *Dianthus* known to the inventor.

2 Drawing Sheets

Genus: *Dianthus.*
Species: ×*hybrida.*
Denomination: 'BRIGHT EYES'.

BACKGROUND OF THE INVENTION

This application claims the benefit of priority under 35 U.S.C. 119(f) of the earlier application for European Community Plant Breeders Rights, Application Number 2007/1925 filed Sep. 3, 2007.

The present invention relates to a new and distinct cultivar of *Dianthus* that is grown for use as a flowering plant for pots and containers and as a hardy perennial for the garden and landscape. The new cultivar is known botanically as *Dianthus×hybrida* and will be referred to hereinafter by the cultivar name 'BRIGHT EYES'.

'BRIGHT EYES' is a complex hybrid plant that is the product of a long term breeding program conducted in a greenhouse environment in Houndspool, Dawlish, Devon, United Kingdom. The primary focus of the breeding program is to produce new cultivars of *Dianthus* that exhibit unique growth habit and flower colors. The inventor selected 'BRIGHT EYES' in 2002 for its double flowers which are colored white with a deep plum red center.

'BRIGHT EYES' resulted from the controlled pollination between an unreleased and unpatented *Dianthus* previously raised by the inventor and known by its code name *Dianthus* 'Tricia' as female parent plant, and an unknown *Dianthus* as male parent plant.

'BRIGHT EYES' is distinguishable from the female parent whose flowers are pale pink with a dark eye. The male parent is unknown and cannot be described.

The varieties of *Dianthus* which are considered by the inventor to most closely resemble 'BRIGHT EYES' are *Dianthus* 'Cranmere Pool' (unpatented) and *Dianthus* 'Lady Madonna' (unpatented). The flowers of 'Cranmere Pool' are more double and are larger than the flowers of 'BRIGHT EYES'. The margins of the flower petals of 'Lady Madonna' are more deeply fimbriated than the margins of the flower petals of 'BRIGHT EYES'. 'BRIGHT EYES' is also a more vigorous plant than 'Lady Madonna'.

Asexual reproduction of the new cultivar was first accomplished by the inventor in 2002 in a cultivated area of Houndspool, United Kingdom. The method of asexual propagation used was vegetative cuttings. Since that time the characteristics of the new cultivar have been determined stable and are reproduced true to type in successive generations.

SUMMARY OF THE INVENTION

The following traits have been repeatedly observed and represent the characteristics of the new *Dianthus* cultivar 'BRIGHT EYES'. These traits in combination distinguish this cultivar from all other commercial varieties known to the inventor. 'BRIGHT EYES' has not been tested under all possible conditions and phenotypic differences may be observed with variations in environmental, climatic and cultural conditions, however, without any variance in genotype.

1. 'BRIGHT EYES' exhibits a compact habit.
2. 'BRIGHT EYES' blooms profusely.
3. 'BRIGHT EYES' exhibits double flowers that are predominantly white in color with deep plum-red centers.
4. 'BRIGHT EYES' blooms from April through October.
5. 'BRIGHT EYES' exhibits grey-green foliage.
6. At maturity, the height of the foliage mound of 'BRIGHT EYES' is 50 cm to 60 cm; the width is 35 cm to 40 cm.
7. 'BRIGHT EYES' is perennial and is hardy to −15° C.
8. 'BRIGHT EYES' is suitable for use as a flowering plant in pots and containers.

BRIEF DESCRIPTION OF THE DRAWINGS

The accompanying color drawings illustrate the overall appearance of 'BRIGHT EYES' showing colors as true as it is reasonably possible to obtain in colored reproductions of this type. Colors in the drawings may differ from the color values cited in the detailed botanical description, which accurately describe the actual colors of the new variety 'BRIGHT EYES'.

The drawing labeled as FIG. 1 depicts an entire flowering plant.

Figure 1:
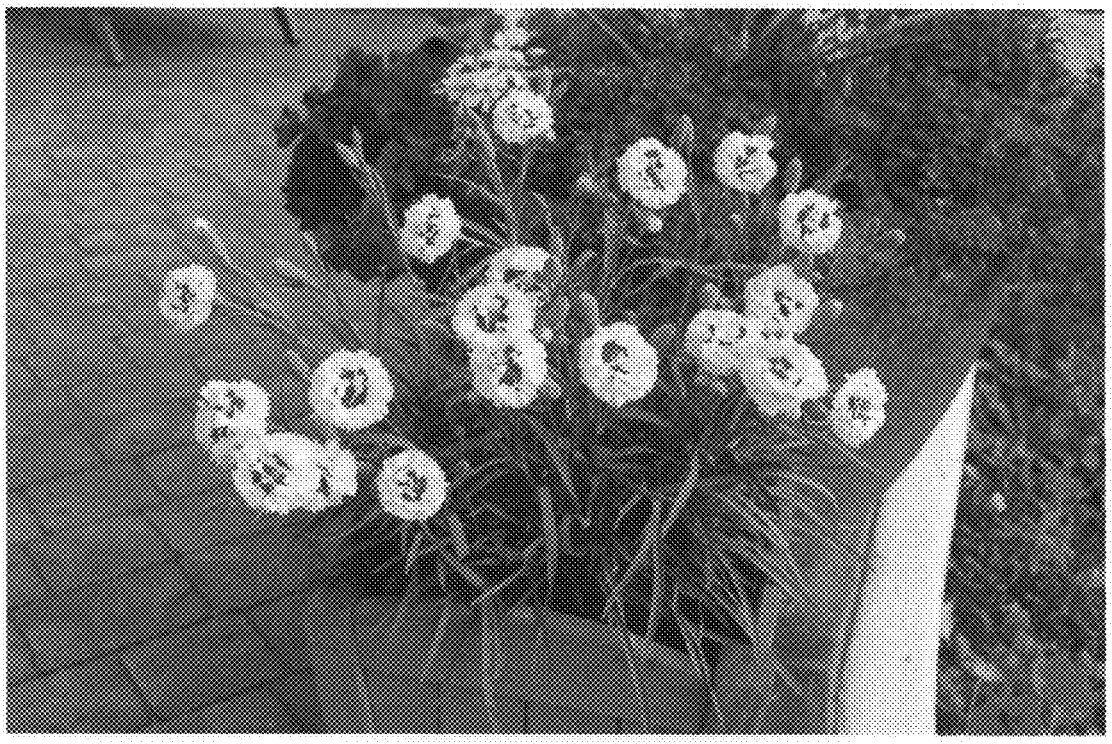
Figure 2:
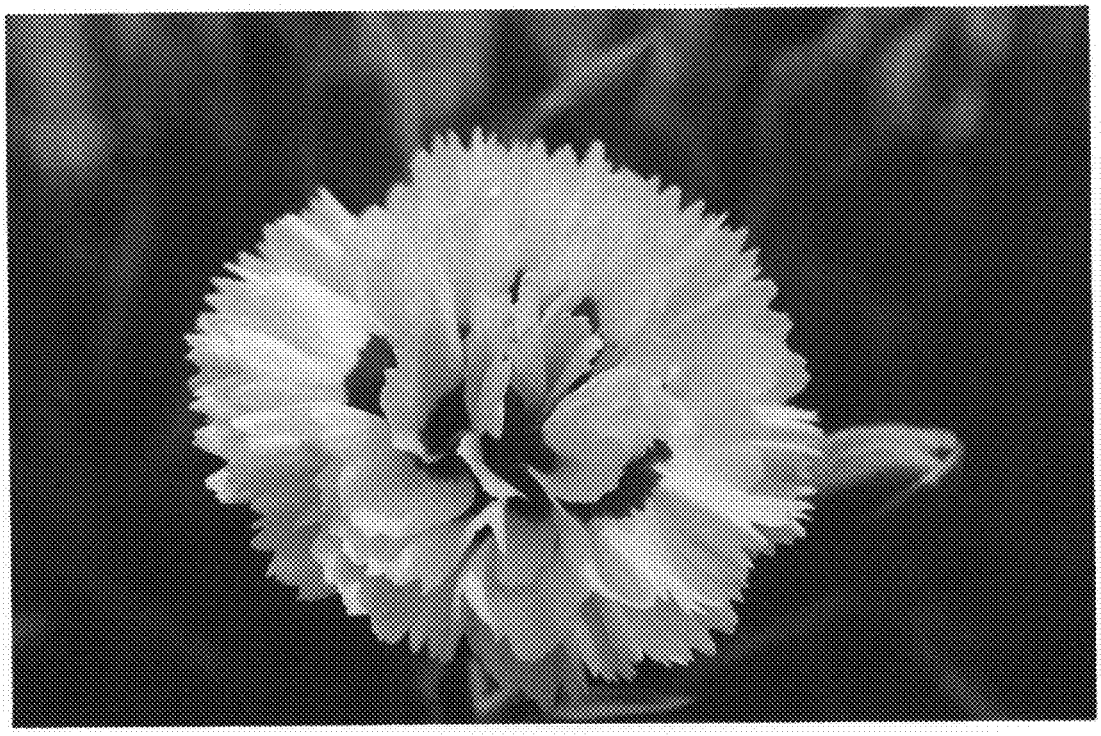

The drawing labeled as FIG. 2 depicts a close-up view of the flower.

All drawings were made of plants grown in 1.5-litre containers in a cold (unheated) glasshouse in Devon, United Kingdom. No chemicals were used to treat the plants. All drawings were made using conventional techniques and although colors may appear different from actual colors due to light reflectance they are as accurate as possible by conventional photography.

DETAILED BOTANICAL DESCRIPTION OF THE PLANT

The following is a detailed description of the new cultivar 'BRIGHT EYES'. Data was collected in spring from 1.5-litre container plants in spring, which were growing in a cold (unheated) glasshouse in Devon, United Kingdom. The color determinations are in accordance with the 2007 edition of The Royal Horticultural Society Colour Chart of the Royal Horticultural Society, London, England, except where general color terms of ordinary dictionary significance are used. The colors of stems, leaves, calyx, and epicalyx have been noted on plants which retain the characteristic waxy bloom of *Dianthus.* No chemicals were used to treat the plants.

Botanical classification: *Dianthus* 'BRIGHT EYES'.

Species: ×*hybrida.*

Common name: Garden pink.

Commercial classification: *Dianthus* hybrid.

Type: Perennial.

Use: Used as a flowering plant for pots and containers and for planting in the garden or landscape.

Parentage: 'BRIGHT EYES' is a complex hybrid plant that resulted from the induced open pollination between the following parent plants:

*Female parent plant.*—*Dianthus* 'Tricia'.

*Male parent plant.*—Unknown.

Plant description:

*Bloom period.*—April through October.

*Plant habit.*—Compact mound with many branches and stems; upright growth.

*Plant height.*—50 cm to 60 cm after 8 months.

*Plant width.*—35 cm to 40 cm after 8 months.

*Plant hardiness.*—Hardy to minus 15° Centigrade.

*Root system.*—Fine fibrous roots.

*Propagation.*—Propagation is accomplished using vegetative cuttings.

*Cultural requirements.*—Grow in full sun, with moderate water, and well-drained moderately fertile soil. Remove dead flower heads to maintain flowering.

*Diseases and pests.*—Susceptible to known *Dianthus* pests and disease but no other susceptibilities to pests or disease are known to the inventor.

*Time and temperature needed to produce a rooted cutting.*—3 weeks are needed to produce roots on cuttings using a mist propagation unit with bottom heat of 21° Centigrade, and a minimum air temperature of 15° Centigrade.

*Crop time.*—3 months starting in the early spring through summer and 6 months starting in the fall is needed to produce a finished container size plant from a well-rooted cutting.

Stem:

*Shape.*—Cylindrical.

*Stem dimensions.*—20 cm to 25 cm in height and 3 mm to 4 mm in diameter.

*Stem surface.*—Glabrous and glaucous.

*Stem color.*—145B.

*Branching.*—Numerous shoots from the axils of the lower leaves.

*Internode length.*—15 mm to 20 mm between nodes.

*Node color.*—145B.

*Node dimensions.*—4 mm to 5 mm in length and 4 mm in diameter.

Foliage:

*Type.*—Evergreen.

*Shape.*—Linear and straight.

*Division.*—Simple.

*Apex.*—Acute.

*Base.*—Decurrent.

*Venation.*—Not Prominent.

*Margins.*—Entire.

*Attachment.*—Sheathing.

*Arrangement.*—Opposite and spiraling.

*Surfaces* (*adaxial and abaxial*).—Glaucous.

*Leaf dimensions.*—100 mm to 120 mm in length and 4 mm in width.

*Leaf color* (*adaxial and abaxial surfaces*).—189B.

*Fragrance.*—Absent.

Flowers:

*Inflorescence.*—Cymose.

*Number of flowers per stem.*—From 3 to 5.

*Peduncle dimensions.*—50 mm to 55 mm in length and 3 mm in width.

*Peduncle strength.*—Erect.

*Peduncle color.*—133B to 133C.

*Flower development.*—In sequence from the uppermost bud.

*Flower type.*—Salviform and symmetrical.

*Flower shape.*—Circular.

*Flower profile.*—Reflexed.

*Flower dimensions:* (*including calyx*).—45 mm in length and 40 mm in width.

*Fragrance.*—Medium: noticeably clove-like but not intense.

*Petals.*—Number: 15–20 petals. Profile, upper part of corolla: Convex. Profile, lower part of corolla: Concave. Arrangement: Persistent, double, apopetalous, overlapping. Margin: Crenate-dentate with 1 mm to 2 mm indentations. Texture: Soft. Shape: Obdeltoid. Surface: Glabrous. Dimensions: 40 mm to 45 mm in length and 25 mm to 30 mm in width. Color (adaxial surface): Ground color of blade: NN155D. Band across blade: 59B. Middle of strap: 145C Base of strap: 145D. Color (abaxial surface): Ground color of blade: NN 155D. Band across blade: Absent. Middle of strap: 145C. Base of strap: 145D. Calyx: Shape: Cylindrical. Longitudinal profile: Flat. Dimensions: 30 mm in length and 10 mm to 12 mm in diameter. Sepals: Fused. Number of sepals: 5. Sepal surface: Glaucous. Sepal color (both surfaces): N138D. Anthocyanin: Absent. Splitting: Not observed. Epicalyx: Bracts: 1 pair of 2. Shape of outer lobe: Acuminate. Dimensions: 14 mm in length and 13 mm in width. Color: 139A on the tip, otherwise 143C. Anthocyanin: Absent. Bracteoles: Number: 2. Dimensions: 10 mm in length and 6 mm in width. Color: 139A on the tip, otherwise 143C. Anthocyanin: Absent. Lastingness of flower: Each individual flower lasts an average of 10 days at 20° C. on the plant.

Reproductive organs:

*Stamens.*—Number: 10–15. Dimensions: 25 mm–30 mm in length and 1 mm in diameter. Color: NN155D.

*Anthers.*—Number: 10–15. Dimensions: 5 mm in length and 1 mm in diameter. Color: 84C. Attachment: Basifixed. NB: For this crop, we have observed that the majority of the anthers are malformed, but occasionally produce pollen.

*Pollen.*—Present. Color: 157A.

*Style.*—Number: 2. Shoulder: Absent. Color: NN155D. Dimensions: 30 mm to 35 mm in length and 1 mm in width.

*Stigma.*—Number: Single. Color: 64D. Dimensions: 5 mm to 10 mm above petals at maturity.

*Ovary.*—Position: Superior. Dimensions: 10 mm in length and 6 mm in diameter. Shape: Spindle. Color (adaxial): 145B. Color (abaxial): 145C.

Seed: Not observed.

It is claimed:

1. A new and distinct cultivar of *Dianthus* plant named 'BRIGHT EYES' as described and illustrated herein.

* * * * *